United States Patent [19]  [11] 3,930,947
Morinaga et al.  [45] Jan. 6, 1976

[54] METHOD OF PRODUCING MICROBIAL CELLS FROM METHANE

[75] Inventors: Yasushi Morinaga; Shigeru Yamanaka, both of Yokohama; Yoshio Hirose, Fujisawa, all of Japan

[73] Assignee: Ajinomoto Co., Inc., Tokyo, Japan

[22] Filed: Dec. 18, 1974

[21] Appl. No.: 534,144

[30] Foreign Application Priority Data
Dec. 26, 1973  Japan.................................. 49-1201

[52] U.S. Cl................... 195/28 R; 195/115; 195/96
[51] Int. Cl.$^2$............................................. C12B 1/00
[58] Field of Search..................... 195/28 R, 96, 115

[56] References Cited
UNITED STATES PATENTS
3,354,047  11/1967  Hitzman............................ 195/28 R
3,649,459  3/1972  Wolnak et al................. 195/28 R X Primary Examiner—Lionel M. Shapiro
Assistant Examiner—R. B. Penland
Attorney, Agent, or Firm—Cooper, Dunham, Clark, Griffin & Moran

[57] ABSTRACT

A novel strain belonging to genus Methylomonas grows well on a culture medium in the presence of methane as the main carbon source. The microbial cells are useful as a feedstuff.

6 Claims, No Drawings

METHOD OF PRODUCING MICROBIAL CELLS FROM METHANE

BACKGROUND OF THE INVENTION

This invention relates to a method of producing microbial cells utilizing methane as the main carbon source.

Methane is one of the most inexpensive carbon sources for microbial growth. It is known that there are many microorganisms capable of growing on a culture medium in the presence of methane as the principle carbon source. However the growth of the most known strains is quite low and unsatisfactory. With mixed cultures, superior growth strains are known. But when the strains are isolated, this superior property of the original strain mixture is somehow lost (Applied Microbiology, 15, 1473–1478 (1967) and 21, 511–515 (1971)). With pure cultures, superior strains, capable of good growth, are not known. Since it is difficult to maintain stable mixed cultures during a large number of cycles, the industrial production of single cell protein from methane is a problem.

THE INVENTION

It is now been found that a novel strain belonging to genus Methylomonas which was isolated from soil grows well as a pure culture on a medium in the presence of methane as a main carbon source.

The new strain is Methylomonas sp AJ-3670 (FERM P-2400), which has been deposited with the Fermentation Research Institute, Agency of Industrial Science and Technology, Ministry for Industrial Trade and Industry, Chiba, Japan, and is freely available from the Institute.

The new strain is characterized by the following properties: Morphological characteristics: (cultivated by shake culture in the presence of methane as the sole carbon source for 18 hours in inorganic liquid medium at 30°C) Unicellular rods, size 1.0–1.2 × 2.0–3.5 $\mu$, motile by means of polar flagella, gram negative, but sometimes cells are partially positively stained in the early growth phase. Sometimes rosettes are formed. Spores or cysts are not formed.

(Cultivated on inorganic agar slant in an atmosphere composed of methane as the sole carbon source for 24 hours). Rods, sometimes show pleo morphism, size 1.0–1.2 × 3–6 $\mu$. Cells stick together by slimy substances and sometimes branched like shapes are recognizable. Granular substances, which are easily stained by Sudan black are recognizable in the cells, spores or cysts are not formed.

Type of agar colonies: (cultivate on inorganic agar plate in the presence of methane for 16 days) diameter 1.0 mm, circular, flat, smooth, entire, butyrous, white buff, opaque. Do not produce soluble pigment.

(Nutrient agar plate) Do not grow.

Physiological characteristics: Catalase positive. Oxidase positive in young culture, but oxidase activity is easily lost in older culture. Nitrate is reduced to nitrate. Optimum growth temperature, 35–37°C, no growth at 40°C. Optimum growth pH 6.0–7.5. Aerobic.

Utilization of organic compounds as a sole carbon source:

Methane is the only one utilizable organic carbon source among the various organic compounds tested. Alcohols, such as methanol or ethanol, aldehydes, such as formaldehydes or acetaldehyde, alkylamines, such as methylamine or ethylamine, organic acids such as formate, acetate, citrate, succinate, pyruvate, oxalate or gluconate, carbohydrates, such as D-glucose, fructose, sucrose, D-ribose, D-xylose, lactose, D-galactose, L-rhamnose, D-arabinose, D-maltose or D-mannose, and natural organic nutrients such as soluble starch, yeast extract, peptone, casamino acids, corn steep liquor or soybean hydrolizates are not utilized. The effects of various organic compounds on the growth of strain FERM P-2400 in the presence of methane are as follows: Methanol, ethanol, formaldehyde, acetaldehyde methylamine, ethylamine, formate, citrate pyruvate and nucleotides have inhibitory effects. D-glucose, fructose, D-xylose, lactose, D-galactose, D-arabinose and D-mannose have no effect. D-ribose stimulates the growth. Casamino acids, corn steep liquor and soybean hydrolyzate have no effect on growth, but yeast extract and peptone stimulate the growth. The above mentioned results were obtained by the following experimental methods. The various substances under test send us 0.1 % alcohols, carbohydrates, organic acids and natural organic nutrients such as yeast extract were added to the inorganic liquid medium. The test culture were shaken for from 2 to 4 days at 30°C after inoculation of bacteria. The growing cultures were tested for carbon assimilation tests and effects of organic compounds on the growth under an atmosphere of methane. With aldehydes and alkylamines, 0.05% was used as the concentration in the above experiments. The composition of the utilized in the morphological observations, utilization of organic compounds and other tests described above was as follows:

| Inorganic synthetic medium | | |
| --- | --- | --- |
| $(NH_4)_2SO_4$ | 0.5 | g/l |
| $KH_2PO_4$ | 0.3 | g/l |
| $Na_2HPO_4.12H_2O$ | 1.8 | g/l |
| $MgSO_4.7H_2O$ | 0.2 | g/l |
| $FeSO_4.7H_2O$ | 10 | mg/l |
| $CuSO_4.5H_2O$ | 1.0 | mg/l |
| pH 7.2 | | |

Cultivation with methane was carried out in the atmosphere of 20% methane and 80% air. The ordinary physiological tests, used for the identification of the ordinary bacteria, for example, the methylred test, and tests for the production of hydrogen sulphide or acid production from carbohydrate, were investigated by the usual methods. However no growth was observed for the methane-oxidizing bacterium of this invention, and the expected results were not obtained.

With methane oxidizing bacteria, there is official classification system. However, the classification system proposed by R. Whittenbury et al. (Journal of General Microbiology, 61, 205–218 (1970) is most widely recognized. In the system, the morphological characteristics of methane oxidizing bacteria are divided into five groups. There are Methylosinus, Methylocystis, Methylomonas, Methylobacter, and Methylococcus.

The characteristics of the present strain were compared with the resort of R. Whittenbury, and the strain is considered to belong to genus Methylomonas. The strain does not belong to genus Methylosinus because it does not form exospore. Nor does it belong to genus Methylocystis because of its motility characteristics. Since the shapes of the cells are rod like, the strain does not belong to genus Methylococcus.

The remaining two genera are divided based on shapes of cyst, and as to the other morphological characteristics, those of Methylomonas methanica and Methylobacter chroococcum are only disclosed in the report. According to the disclosure, the key characteristics of genus Methylobacter are to form cyst of azotobacter type and the similarity to the large-cell-forming species of Azotobacter. On the other hand, as to genus Methylomonas, some strains form no cyst, an do not show pleomorphism. These characteristics are summarized in Table 1. Thought the present strain shows some pleomorphism on an inorganic agar slant, it does not show pleomorphism nor form cyst in a liquial culture medium. Moreover, shape of cells is not varied on continued subculture. These facts indicate that the strain belongs to genus Methylomonas. The characteristics of the strain were compared with those of all of the species of the genus Methylomonas disclosed in the report. Since the characteristics of the strain were found to be different from those of the known strain, the present strain is considered to be a novel strain, namely Methylomonas sp. FERM P-2400. As appears from Table 2, the known strains which are capable of growing at a temperature of 37°C are Methylomonas albus and Methylmonas agile. The strain of this invention is also capable of such growth. The known strains are different from the strain of this invention in assimilation of methanol. Assimilation of methanol is regarded as a significant factor for the classification of methane oxidizing bacteria. The present strain, not only does not assimilate methanol. Instead its growth is strongly inhibited by methanol in concentration of 0.1%. When compared with characteristics of whole strains of genus Methylobacter described in Table 2, it is clear that there is no strain of genus Methylobacter corresponding to the present strain.

In the report of R. Whittenbury, Methanomonas methanooxidans is not mentioned. However L. R. Brown et al. (*Canadian Journal of Microbiology*, 10, 791–799 (1964)) and P. K. Stocks et al. (*Journal of Bacteriology*, 88, 1071–1077 (1964)) indicated that Methanomonas methanooxidans can assimilate methanol. Therefore, the present strain does not belong to Methanomonas methanooxidans.

The culture media employed for growing cells of this bacterium contain at least one assimilable nitrogen source and inorganic salts. The presence of suitable amount of organic nutrients, such as peptone and yeast extract, may promote microbial growth. The culture medium is placed in a culture vessel which can be sealed, sterilized and inoculated with an inoculum of the present strain. Methane and oxygen gases are introduced into the vessel in the conventional manner. One to five percent by weight of carbon dioxide gas is preferably added together with the two gases mentioned as above, because the suitable amount of the gas may shorten the lag phase of growth.

The source of methane is not limited. Natural gas, the gas produced by methane fermentation under anaerobic conditions and other conventional sources may be utilized. The oxygen gas source may be pure gas or air.

The necessary amounts of each gas may first be sealed into the vessel and replaced by fresh gases in a batchwise operation during fermentation. Alternatively each gas may be continuously supplied by conventional aeration the gases may be suppled separately or in a mixed form.

Typical nitrogen sources include ammonium salts, such as ammonium sulfate and ammonium chloride, nitrates, such as potassium nitrate and ammonium nitrate, aqueous ammonia, and ammonia gas. During fermentation, the concentration of ammonium salts is preferably maintained at 0.03 to 0.2 %.

The inorganic salts are those employed in conventional operations, and include, for example, potassium phosphates, magnesium sulfate, ferrous sulfate and copper sulfate.

The cultivation is carried out for 1 to 7 days, while the temperature is maintained at 20° to 38°C. The pH of the medium is generally held at 5 to 8. When ammonium salts are employed as the nitrogen source, ammonia in the culture medium is consumed during cultivation with the result that the pH of the medium decreases. In this case, it is necessary to add alkaline materials, such as ammonia, to the medium during cultivation.

The bacterial cells may be recovered from the fermentation broth by the usual techniques, such as centrifuging or filtering.

Since the bacterial cells produced in the invention contain a significant amount of protein, they are useful as feedstuffs, food and so on. The protein may be extracted from the cells by conventional procedures.

The invention is further illustrated by the following non-limiting Examples.

EXAMPLES 1

20 Ml of an aqueous culture medium containing:

| | | |
|---|---|---|
| $(NH_4)_2SO_4$ | 0.5 | g/l |
| $KH_2PO_4$ | 0.3 | g/l |
| $Na_2H PO_4.12H_2O$ | 1.8 | g/l |
| $MgSO_4.7H_2O$ | 0.2 | g/l |
| $FeSO_4.7H_2O$ | 10 | mg/l |
| $CuSO_4.5H_2O$ | 1.0 | mg/l |
| pH 7.2 | | | was placed in a 500 ml shake flask, and sterilized. The medium was inoculated with Methylomonas sp. FERM P-2400. The air in the flask was replaced by a mixed gas composed of 20% methane and 80% air, and then the flask was sealed. The inoculated medium was held at 36.5°C for 25 hours with shaking. For the first 20 hours, the strain grew logarithmically at the specific growth rate of 0.17 $hr^{-1}$.

After the cultivation, the bacterial cells were collected by centrifuging, washed and dried. Dry cell material in an amount of 0.6 g/l was obtained. The nitrogen content of the dry cell was 10.4%, and crude protein content was about 65%, respectively.

EXAMPLE 2

400 Ml of the aqueous culture medium containing the same constituents as in Example 1 and yeast extract at a concentration of 0.5 g/l was placed in a one liter glass jar fermenter and sterilized. The medium was inoculated with 20 ml of a seed culture of Methylomonas sp. FERM P-2400 prepared as in Example 1, and cultured at 36.5°C for 48 hours with stirring (1,200 r.p.m.) while methane gas in the rate of 30 ml/min and air in the rate of 170 ml/min were bubbled into the medium. During cultivation, the pH of the medium was maintained at 6.6 using ammonia gas. For 36 hours, the strain grew logarithmically at the specific growth rate of 0.2 $hr^{-1}$. The concentration of the bacterial cells after 36 hours was 8.2 g/l.

After the cultivation, the bacterial cells were collected and 16.8 g/l of dry cell material was obtained.

EXAMPLE 3

In the same way as in Example 2, a culture medium was prepared and cultured. After 30 hours (4.8 g/l as dry cell weight), the culture broth was gradually diluted by the fresh medium in the dilution rate of 0.15 hr$^{-1}$. After 18 hours from the biginning of the dilution, the culture broth reached a stationary state containing 4.3 g/l (as dry cell weight) of the bacterial cells. The yield based on the consumed methane was 66%.

Table 1

| Genus | Resting Stage Shape of Cells | | Morphological Change |
|---|---|---|---|
| Methylomonas | Immature Azotobacter-type cyst * | Rod | Do not show marked pleomorphism |
| Methylobacter | Azotobacter-type cyst | Rod | Show similarity to the large-cell-forming species of Azobacter |
| The present strain | Not recognized | Rod | No morphological change in a liquid medium, but pheomorphism is recognized on agar medium |

* not all strains form an identifiable resting stage

Table 2

| Strain | Growth at 37°C | Assimilation of 0.1% Methanol | Stimulation of Growth by Yeast Extract | Motility | Color of Colony | Production of Soluble Pigment |
|---|---|---|---|---|---|---|
| The present strain | + | − | + | + | White to Buff | − |
| Methylomonas methanica | − | + | + | + | Ochre to Pink | Green |
| M. albus | + | + | + | + | White | − |
| M. streptobacterium | − | − | − | − | White | − |
| M.agile | + | + | + | + | White | − |
| M.rubrum | − | + | − | + | Red | − |
| M.rosaceus | − | − | − | + | Pale pink | − |
| Methylobacter chroococcum | − | − | − | − | Pale pink | − |
| M.bovis | + | − | − | − | White to Brown | Yellow |
| M.capsulatus | − | − | − | + | White to Brown | − |
| M.vinelandii | + | − | − | + | White to Brown | − |

What is claimed is:

1. A method which comprises culturing Methylomonas sp. FERM P-2400 in an aqueous culture medium containing an assimilable nitrogen source and inorganic salts, in the presence of methane as the major carbon source, until the cells of said strain multiply in said culture medium, and recovering the multiplied cells from said medium.

2. A method as in claim 1, wherein said methane constitutes the sole significant source of assimilable carbon in said medium.

3. A method as in claim 1 including the addition of from 1% to 5% by weight of carbon dioxide.

4. A method as in claim 1 carried out in a batchwise manner.

5. A method as in claim 1 carried out in a continuous manner.

6. A method as in claim 1 wherein yeast extracts or peptone are utilized as an additional carbon source.

* * * * *